United States Patent
Nussinovitch et al.

(10) Patent No.: US 6,299,915 B1
(45) Date of Patent: *Oct. 9, 2001

(54) PROTECTIVE COATING FOR FOOD, METHOD FOR PRODUCING SAME AND PRODUCTS COATED BY SAME

(75) Inventors: Amos Nussinovitch, Petach Tikva; Varda Hershko, Rehovot; Haim D. Rabinowitch, Kyriat Onu, all of (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/521,959

(22) Filed: Mar. 9, 2000

Related U.S. Application Data

(63) Continuation-in-part of application No. 08/836,602, filed as application No. PCT/US95/14252 on Nov. 1, 1995, now Pat. No. 6,068,867.

(30) Foreign Application Priority Data

Nov. 2, 1995 (IL) ......................................................... 111495

(51) Int. Cl.⁷ .................................. A23B 7/16; A23L 1/05
(52) U.S. Cl. .............................. 426/89; 426/93; 426/102; 426/303; 426/310; 426/573; 426/575; 426/615; 426/654

(58) Field of Search ..................................... 426/102, 573, 426/575, 303, 304, 310, 615, 616, 654, 89, 93

(56) References Cited

U.S. PATENT DOCUMENTS

| | | | |
|---|---|---|---|
| 5,128,159 | 7/1992 | Sayles | 426/310 |
| 5,156,866 | 10/1992 | Sato et al. | 426/5 |
| 5,198,254 | 3/1993 | Nisperos-Carriedo et al. | 426/102 |
| 5,376,391 | 12/1994 | Nisperos-Carriedo et al. | 426/102 |
| 6,068,867 | * 5/2000 | Nussinovitch et al. | 426/102 |

* cited by examiner

*Primary Examiner*—Arthur L. Corbin
(74) *Attorney, Agent, or Firm*—Browdy and Neimark

(57) ABSTRACT

The invention relates to a hydrocolloid protective coating for food and/or agricultural products comprising:

- 5–95% dried hydrocolloid gel;
- 0.2–50% of one or more natural compounds isolated from the surface of said product or a compound substantially equivalent thereto;
- 4–30% of water; and
- optional additives.

The protective coating provides improved protection of the product, thereby extending its shelf-life. A method for producing the coating, and food and agricultural products protected by the coating are also disclosed.

17 Claims, 4 Drawing Sheets

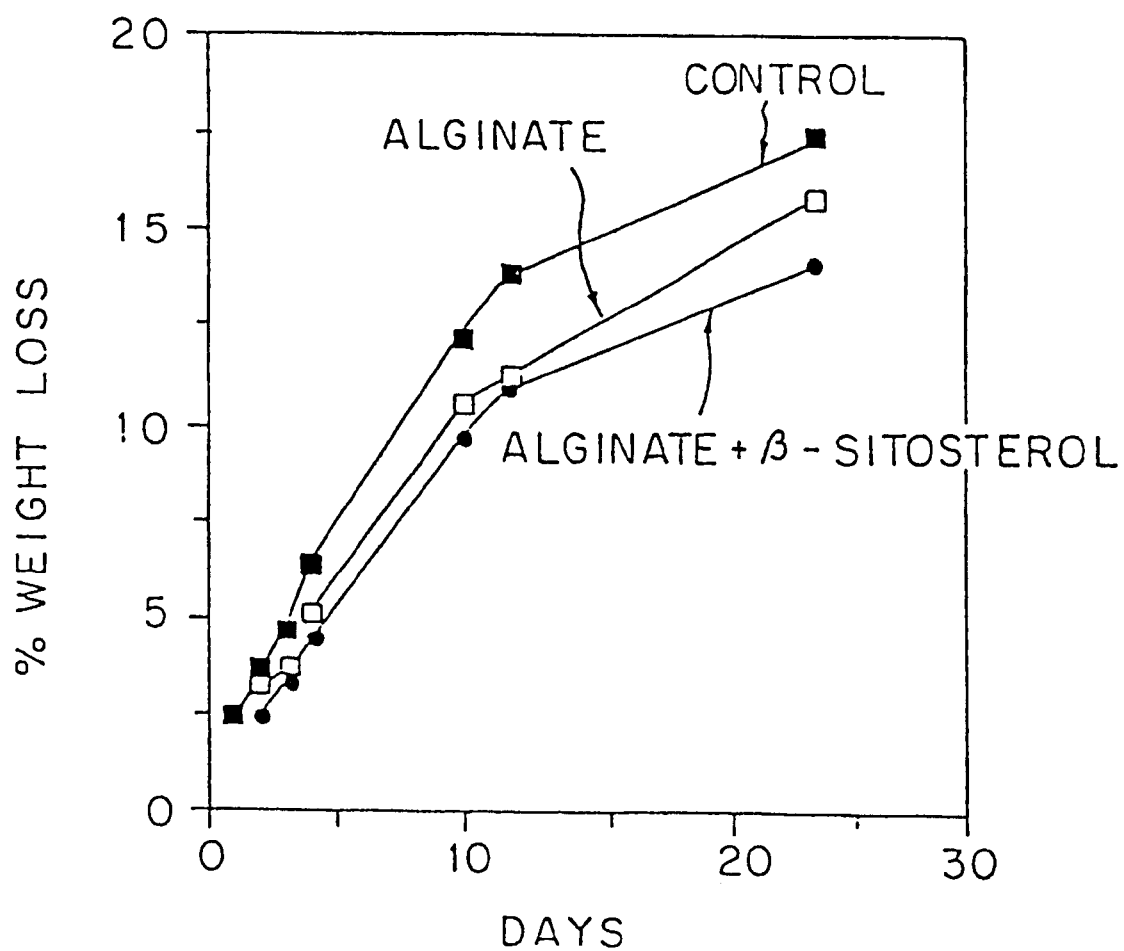

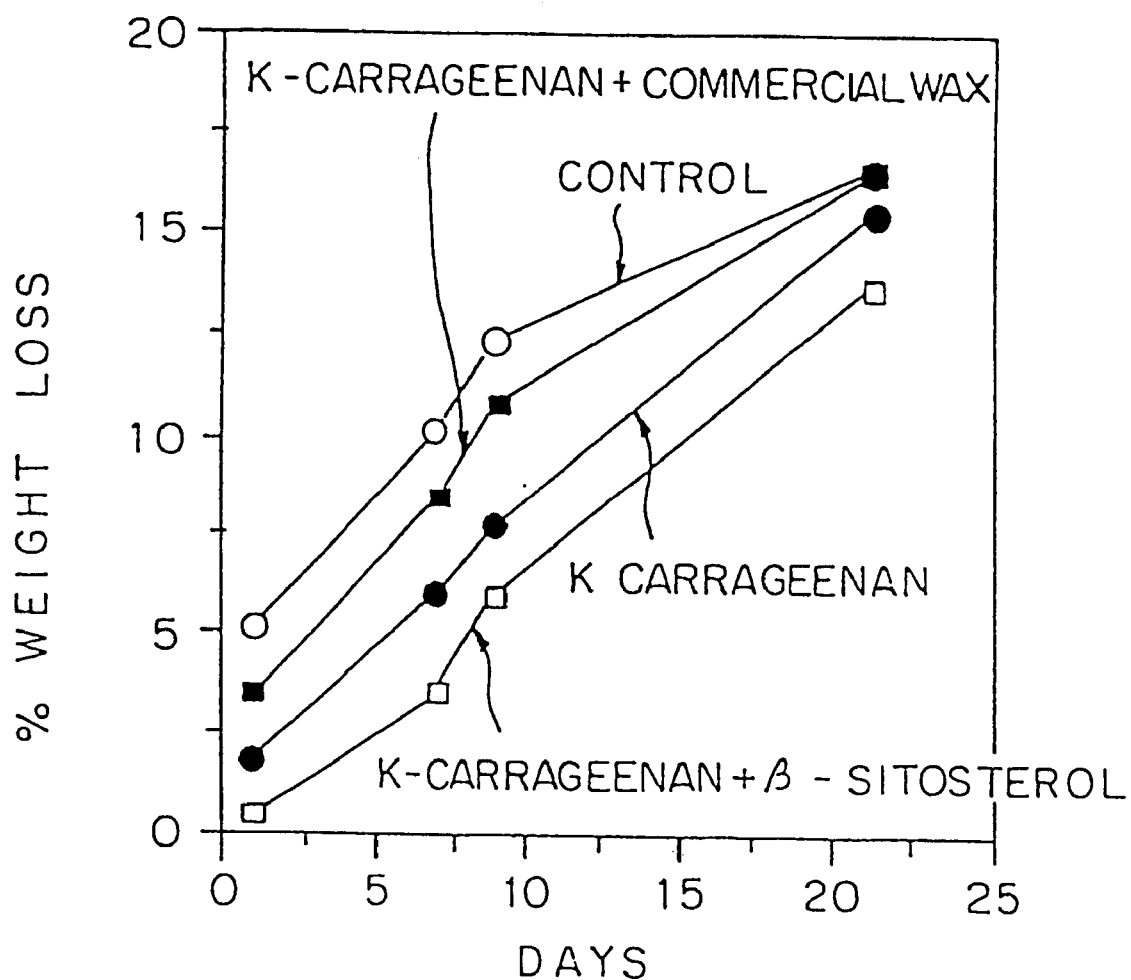

PROTECTIVE COATING FOR FOOD, METHOD FOR PRODUCING SAME AND PRODUCTS COATED BY SAME

This is a CIP of parent application Ser. No. 08/836,602 filed Jul. 14, 1997 now U.S. Pat. No. 6,068,867 having an International filing date as PCT/US95/14252 of Nov. 1, 1995 the contents of which are hereby incorporated by reference.

FIELD OF THE INVENTION

The invention relates generally to the preservation of food and agricultural products. More particularly, the invention relates to a hydrocolloid protective coating which provides improved protection of the food and/or agricultural product, thereby extending its shelf-life.

The invention also relates to other aspects, e.g. to a method for producing the protective coating and to food and agricultural products protected by such coating.

BACKGROUND OF THE INVENTION

The need to prolong shelf-life of food products, in particularly fresh produce, without harming quality, is well recognized. Many coating formulations are disclosed in the literature.

One of the known methods for coating fresh produce such as onions and edible fungi is to form a coating by applying to the exterior surfaces of onions or fungi a gelation solution comprising a hydrocolloid such as sodium alginate, and cross linking the hydrocolloid on the surface by a solution comprising a gelation inducing agent, such as $CaCl_2$.

The so-obtained coating is both biodegradable and edible, and provides a protective coating to the treated vegetable. U.S. Pat. No. 3,865,962 discloses a process for coating raw onion products by immersion of the onion in an aqueous dispersion containing water soluble algin and subsequently treating the coated onion with an aqueous calcium ion to induce gelation.

EP 277 448 discloses an edible coating containing gelatin and polysaccharide. A cross-linking agent containing calcium ions is used for obtaining the coating.

U.S. Pat. Nos. 5,198,254 and 5,376,391 are directed to increasing the stability of fruits, vegetables and fungi by coating same with a composition comprising a polysaccharide polymer, a preservative an acidulant and two emulsifiers including lecithin, as well as optionally at least one antioxidant, a plant growth regulator and/or a chilling injury protectant. The polysaccharide polymer is preferably carboxymethylcellulose, but instead may be another hydrocolloid. Regardless, the polysaccharide polymer, even if a hydrocolloid, is not of the type which can undergo gelation without a gelation inducing agent, and these patents only involve drying of the coating composition on the product to be protected, and never gelation.

Moreover, none of the prior art documents discloses a coating containing in its matrix a compound having a specific reference to the surface of the product to be coated.

SUMMARY OF THE INVENTION

It is therefore an object of the present invention to provide an improved protective coating for food and agricultural products.

A more specific object is to provide a coating tailored to the specific food or agricultural product.

Another object of the invention is to control the hydrophobicity of the coating and its chemical compatability to the skin surface, thereby improving adhesiveness to the product and thus resulting in better control of the modulated atmosphere surrounding the coated product.

The invention provides a protective coating for food or agricultural product comprising 5–85% dried hydrocolloid gel, together with 0.2–50% of at least one natural compound isolated from the surface layers of said product which provides a protective function, i.e. a protective natural compound, or at least one protective compound substantially similar thereto. By "compound substantially similar thereto", what is meant is a chemical compound, whether natural or synthetic, which has both (1) a chemical structure similar to the chemical structure of the natural compound isolated from or found in the surface layers of the product, and (2) a protective function which is not substantially less than the protective function of said natural compound. Once the natural protective compound has been isolated and identified chemically structurally similar compounds can then be routinely tested for their protective activity.

The invention also provides a method for producing a protective coating for food and/or agricultural products comprising applying to the external surface of said product a gelation solution comprising a hydrocolloid and, optionally, a solution comprising a gelation inducing agent, wherein at least one of said solutions further comprises at least one said protective natural compound isolated from the surface layers of said product, or at least one said protective compound substantially similar thereto.

BRIEF DESCRIPTION OF THE DRAWINGS

FIG. 1 is a graph depicting the weight loss of garlic bulbs as a function of time. Garlic bulbs coated by an alginate together with β-sitosterol according to one embodiment of the invention (●) as compared with alginate coating (□) and with no coating—(●).

FIG. 2 is a graph depicting the weight loss of garlic bulbs as a function of time in another embodiment of the invention—garlic bulbs coated by a K-Carrageenan with β-sitosterol (□). Comparison to coating with K-Carrageenan without a further additive (●), to K-Carrageenan together with commercial wax (●) a and to no coating (○) is also depicted.

DETAILED DESCRIPTION OF EMBODIMENTS OF THE INVENTION

Figure 3A:
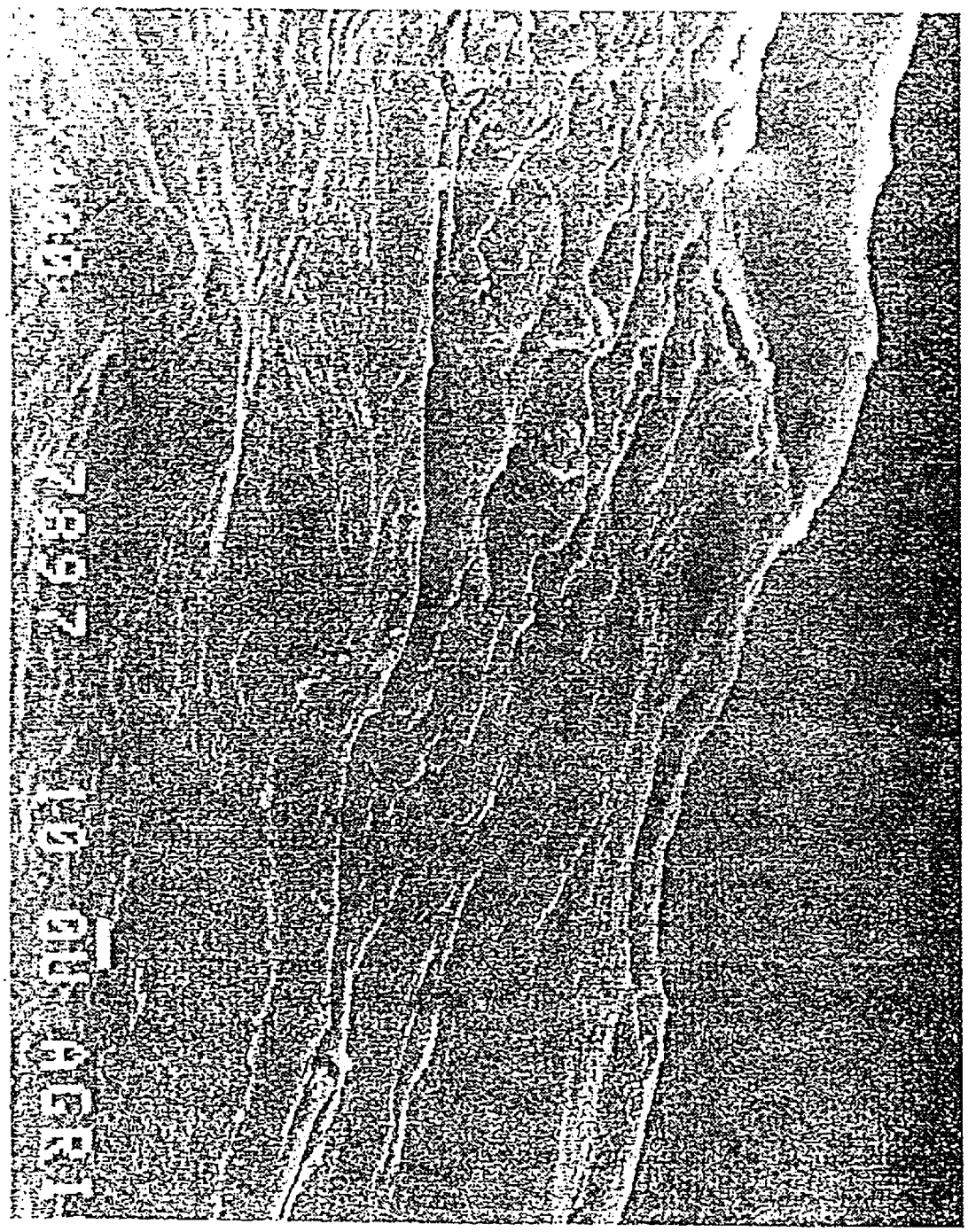
FIG. 3 are electron microscope micrographs of: (a) a skin of garlic bulb coated by a solution containing 2% K-Carrageenan and; (b) a skin of garlic bulb coated by a solution containing 2% K-Carrageenan together with 0.2% β-sitosterol.

As noted above, the invention relates to protecting food and/or agricultural products with a surface coating of a dried gel comprising a hydrocolloid and a protective compound isolated from the product to be protected or from a similar product, or a protective compound substantially similar thereto. The hydrocolloid is desirably one which is capable of undergoing gelation on its own. On the other hand, other hydrocolloids can be used in conjunction with a gelation inducing agent.

Application of a gelation inducing agent is essential to the invention when the hydrocolloid undergoes gelation only in the presence of a gelation inducing agent. However, with hydrocolloids such as agar or gelatin, which undergo gelation without a gelation inducing agent, the application of a solution containing said gelation inducing agent is not required. When needed, the gelation inducing agent can be applied first and the hydrocolloid solution thereafter, or alternatively the hydrocolloid solution is applied first and the gelation inducing agent is applied subsequently thereafter.

It was found that the addition of an agent which reduces the surface tension of the coating causes a better comparability between the coating and the surface free energy of the coated food. An example of such an agent is ethanol, which may be added to the gelation inducing agent, or the food product may be immersed in such agent prior to producing the gel coating on the food and/or agricultural product.

As noted above, the protective natural compound found in or isolated from the surface layers of the product, or the protective compound substantially similar thereto, can be incorporated into the gelation solution comprising the hydrocolloid, or into the gelation inducing agent solution.

The gelation inducing agent may be a cross linking agent, a poly anion, a poly cation, or a mixture thereof. Preferably the gelation inducing agents are chloride salts such as calcium chloride for alginates, potassium chloride for K-carrageenan and magnesium chloride for gellan. Examples of other suitable gelation inducing agents are calcium lactate, calcium stearate, calcium acetate, calcium gluconate and polyphosphates.

The hydrocolloid in the gelation solution may be any known hydrocolloid which may undergo gelation, such as agar, agarose, alginate, gelatin, low methoxy pectin (LMP), chitosan, gellan, K-carrageenan or mixtures of xanthan together with locust bean gum (LBG). Xanthan and locust bean gum are used in combination because in combination they have the ability to gel, whereas each used individually does not have the desired gelling ability.

The protective natural compound isolated from the surface layer of the food or agricultural product, which provides the specific tailoring of the coating to the product, may be a hydrocarbon including terpenes and oleoresins such as balsam and resin, a wax component such as oleic acid, stearic acid or palmitic acid, a sterol such as $\beta$-sitosterol, ergosterol or stigmasterol, a protein such as casein from milk or zein from corn or collagen from meat, a fat such as cocoa butter or lard, squalene (isolated from tomato and from the epicuticular wax of grapefruit); or a mixture thereof.

For example, an essential oil from the skin of an agricultural product may be used as the protective natural compound, such an essential oil comprising one or more of a said hydrocarbon, wax and fat. Such so-called essential oils are commercially available; for example, these oils are available from citrus fruit juice processors e.g. oils which are regularly squeezed from the fruit during the same process when the juice is squeezed from such fruit. When the juice is extracted from the fruit, its compressed peel is washed with water, and the essential oil is separated from the water such as by centrifugation. In general, essential oils are extracted commercially from all citrus fruits and from many other plants, these essential oils.being used conventionally in cosmetics and medicine.

Alternatively, the protective natural compound isolated from the surface of the food or agricultural product to be coated may be substituted by a protective natural product isolated from a different source, subject to being very similar in most physical and chemical properties to a compound present on the surface to be coated. For example, an essential oil extracted from one citrus fruit can be used to protect other types of citrus fruit; stigmasterol extracted from the wax coating of garlic bulbs can be used to protect narcissus bulbs; limonene, an optically active terpene, in its D- or L-forms, or a racemic mixture thereof known as dipentene, present in a large amount in many essential oils, can be used as a protective compound for coating many food and/or agricultural products, as can other terpenes. Yet another alternative is to utilize a protective synthetic compound substantially similar to a protective natural compound present in the surface layer to be coated.

It is indicated above that the protective natural compound is one which is isolated from the surface of a food or agricultural product. What is meant by this language is that the protective natural compound is one which is found in major or minor quantities in the surface layer of the agricultural product in question. However, such protective natural compound can also be found in the interior of the agricultural or food product, and indeed in some cases its concentration within the interior is higher than its concentration on the surface, in which case it makes sense to extract such protective natural compound from within the food or plant. For example, in the case of protecting a food product such as cheese, the protective natural compound can be milk itself, or casein, which is clearly a compound which is not found solely in the "surface".

The coating obtained is a dry film consisting of a matrix of dried hydrocolloid gel with a compound specific to the product to be coated incorporated within said matrix.

The gelation solution may further comprise a known adhesive agent such as natural gums, e.g. locust bean gum (LBG) and gum arabic, polyoxes, cationic water soluble polymers, gelatin, wellan gum, xanthan, guar gum, karya gum or fenugreek. The gelation solution may further comprise emulsifying agents such as lecithin, ethylene glycol monostearate, ammonium lauryl sulfate, sodium steroyl-2-lactylate, potassium oleate, propylene glycol monostearate, sodium alkyl sulfate, oleic acid or polyglycols.

The gelation solution may further comprise a preservative agent, such as potassium sorbate, bisulfite, or sodium benzoate.

According to the invention, the coating can be applied to any food or agricultural product which requires extension of shelf-life such as fruits including grapes, tomatoes, apples, pears, peaches, etc. and also citrus fruits, e.g. grapefruit, oranges, lemons, lime, mandarines, tangerines, tangelos, clementines, etc.; vegetables such as lettuce, cauliflower, broccoli, etc.; cuttings; bulbs such as onions and garlic; tubers such as potatoes etc.; corms of flowers and ornamentals; fungi such as mushrooms; or processed food products, preferably food products containing fatty ingredients, such as cheeses, ice cream cones, or baked goods. The invention extends to food and agricultural products coated in accordance with the invention.

It will be understood that not all protective compounds are appropriate for use with all food and agricultural products. For example, casein is suitable for use as a protective compound for protecting solid food products based on milk e.g. cheese. Cocoa butter is suitable for use in protecting confections. Lard and/or collagen are suitable for use in protecting at least some meat products. Components of vegetable waxes such as oleic acid, palmitic acid and stearic acid are useful for protecting vegetable tissues, and zein is useful for protecting corn and food products based on corn. Based on the present disclosure, those skilled in the art will be able to select appropriate protective compounds for the food or agricultural product to be protected, and any testing required will be at most routine.

Preferably, the hydrocolloid solution comprises between 0.2% to 20% of hydrocoloid and the contents of the protective natural product (e.g. sterol), or the protective compound substantially identical thereto ranges between 0.001% to 5%. The higher the sterol or other protective compound concentration, the better coating is achieved; however, due to the high costs of sterols or other waxy materials suitable for the coating according the the invention, it is preferable to decrease the content of the sterol in the gelation solution and thereby in the coating, so that an optimal coating at reasonable costs is obtained.

The invention is illustrated in more detail by the following non and specific examples with reference to the drawings.

EXAMPLE 1

Coating of fresh garlic heads (bulbs) was performed by immersion of the bulbs in a 2% sodium alginate solution, containing 0.2% (w/w) β-sitosterol, previously dissolved in absolute ethanol. β-sitosterol was purchased from SIGMA. Bulbs were immersed in the solution for 5 to 60 seconds; thereafter, excess of the alginate-sterol solution was allowed to drip for about one minute and the garlic bulbs were then immersed in 2% (w/w) calcium chloride solution for 5 to 60 seconds. The wet film was dried either at room temperature, or under a continuous flux of warm air (60° C.) for 5 minutes. After drying bulbs were stored under 25° C. and 70% relative humidity for further evaluation.

For comparative purposes, garlic heads were treated by the same procedure with a 2% sodium alginate solution devoid of any sterol and subsequently in a 2% $CaCl_2$ solution to produce a known coating.

Control bulbs were left untreated.

The dry film of the coated garlic contains 81% cross-linked sodium alginate, 9% sterol and 10% water.

The fresh weight loss of the treated garlic bulbs was measured as a function of time and depicted in FIG. 1, which shows that after 3 weeks in storage weight loss in control bulbs was 17.3%, weight loss of alginate treated bulbs was by 1.5% less than controls, whereas weight loss of bulbs having a coating of alginate in combination with β-sitosterol was 3.3% lower than control.

It should be noted that a decrease of 3.3% in weight loss means a saving of 33 kg per one ton of garlic bulbs, which is of high commercial significance.

Water vapor permeability of coating was measured using standard test methods for vapor transmission of materials as described in ASTM E-96-93 (1993). Water vapor transmission (WVT) was found to be 540 g/d $m^2$ for alginate coating whereas alginate with.0.2% β-sitosterol decreased the WVT to 450 g/d $m^2$.

Accumulation of carbon-dioxide under the coating was determined by injection of inherent gases, sampled by an appropriate syringe, into Gas Chromatograph (Gow-Mac series 850), equipped with poropack column Q. Accumulation of carbon dioxide is known to improve the shelf life of the vegetable by reducing respiration and acting as ethylene antagonist, thus postponing deterioration of the fresh vegetable. Alginate coated garlic contained 0.315% carbon dioxide after 33 days of storage at 25° C. and 70% RH. Garlic bulbs coated with alginate together with β-sitosterol contained 0.834% carbon dioxide after storage for the same period and under same conditions. Uncoated garlic contained only 0.15% carbon dioxide.

The force required for peeling the coatings produced was measured. Peeling test was performed with a custom made peeling unit attached to Instron 1100 Universal Testing Machine. The peeling device being similar to that described in ASTM D413-82 (2) and SAE J 1600-87. The rate of peeling was 5 mm/min and the peeled area 1 square centimeter.

Peeling of an alginate coating required 11 mN whereas for a coating of an alginate and 0.2% β-sitoterol a force of 13 mN was measured. The higher peeling force indicates better attachment of the coating to the garlic skin; hence the coating containing sterol is more strongly attached and thus more difficultly detached from the natural skin of the garlic thereby ensuring adhesion.

EXAMPLE 2

Great headed garlic bulbs were immersed in a warm solution (50° C.–60° C.) containing 2% K-carrageenan and 0.2 % β-sitosterol for about 5 seconds. Excess of the carrageenan-sterol solution was allowed to drip and the great headed garlic bulbs were then immersed in 2% (w/w) potassium chloride solution. The wet film was dried either at room temperature, or under a continuous flux of warm air and the dried bulbs were stored as described in Example 1.

For comparative purposes, similar bulbs of great headed garlic were treated by the same procedure using a 2% K-carrageenan solution devoid of any sterol, and by a 2% K-carrageenan solution containing commercial wax, such as wax used for waxing avocado and citrus fruit. Control bulbs were left untreated. The fresh weight loss of the great headed garlic bulbs was measured as a function of time and is depicted in FIG. 2, which shows that weight loss of K-carrageenan treated bulbs was by 1.8% less than uncoated controls whereas weight loss of bulbs having a coating of K-carrageenan in combination with β-sitosterol was 3.6% less than control.

K-carrageenan coating with commercial wax was less effective in respect of weight loss, as compared to above mentioned coatings.

Commercially the coating of K-carrageenan in combination with β-sitosterol results in reduced losses of 36 kg per one ton of great headed garlic.

The contents of the dry film is 73% cross-linked K-carrageenan, 7% sterol and 20% water.

Water vapor permeability was measured as described in Example 1. It was found that water vapor transmission WVT for the K-carrageenan coating was 453g/d $m^2$ whereas for the K-carrageenan together with β-sitosterol the WVT decreased to 394 g/d $m^2$.

Accumulation of carbon-dioxide was measured as described in Example 1, was found to be 0.23% for the K-carrageenan coating and 0.4% for the K-carrageenan in combination with β-sitosterol.

Figure 3B:
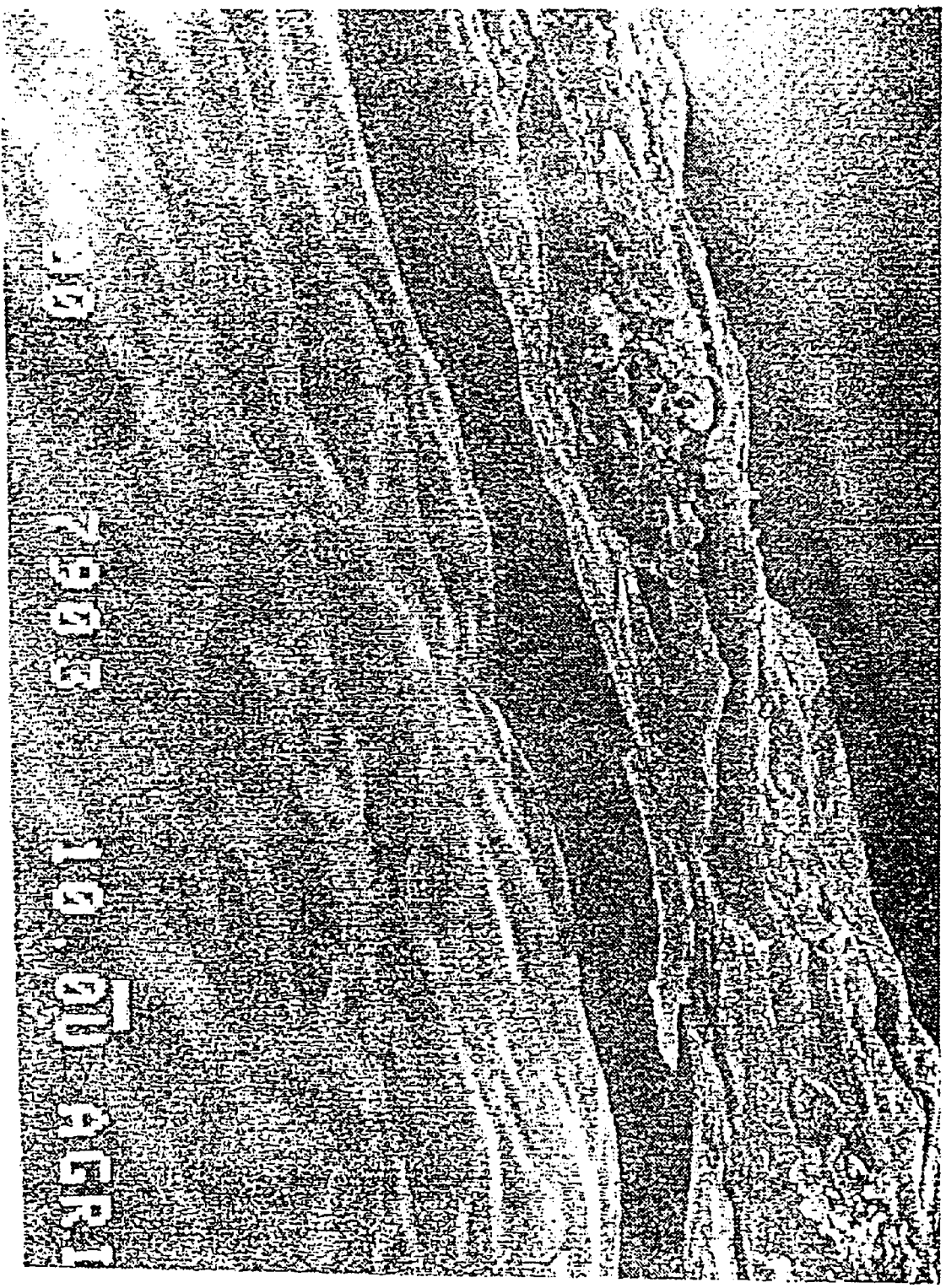

Electron microscope micrographs provide further information on the adhesion of the coating to the natural skin of the great headed garlic. Mean distances between the K-carrageenan coating and the great headed garlic skin were found to be 15 microns, whereas the distance between the hydrocolloid-sterol coating and the skin of the great headed garlic was only 7.8 microns. The electon microscope micrographs of FIG. 3 show clearly the differences in distance.

Analysis of the natural waxes found on the exterior of the great headed garlic, prior to coating, showed its dominant component to be β-sitosterol.

EXAMPLE 3

Dry garlic bulbs (three months after harvest) were immersed in a warm solution (60–70° C.) containing 2% gellan gum (Kelcogel) and 0.01% β-stigmasterol for about 15 seconds. Excess of the gellan-sterol solution was allowed to drip and the garlic bulbs were then immersed in 0.2% (w/w) MgCl$_2$ solution. The gelled layer coating of the garlic was then dried by blowing warm air, and the dried bulbs were then stored as described in Example 1.

For comparative purposes similar dry garlic bulbs were treated in same procedure with 2% gellan solutions. After 40 days of storage in ambient temperature, bulbs coated with gellan lost about 4.2% of their initial weight and those with gellan and sterol lost about 3.5% moisture. Thus, about 17% difference in moisture loss was presented by the coating.

Good mechanical properties of dry films can be achieved by using gellan gum together with sterol. The strength (stress at failure) of this coating was about 20.9 MPa and the strain at failure was 0.046 in average.

The dry film of the gellan-sterol coating contains 91.5% cross-linked gellan, 0.5% sterol and 8% water.

EXAMPLE 4

Garlic bulbs were immersed in 0.5% (w/w) MgCl$_2$ for about 60 seconds to ensure good wetting. The excess of the crosslinking agent was allowed to drip and then the garlic bulbs were immersed in a 1.5% (w/w) gellan solution containing 0.005% β-sitoterol and 0.0025% stigmasterol, both latter compounds of which were previously dissolved in absolute ethanol. Weight difference of 25% in favor of the coated bulbs were found when compared to bulbs coated by the same solutions applied at a different order.

The dry film of the gellan-sterol coating contains 87.5% cross-linked gellan, 0.5% sterols and 12% water.

EXAMPLE 5

Flower bulbs of the narcissus family were immersed in a warm solution (45° C.) of 0.5% agarose containing 0.01% β-stigmasterol and 0.001% of potassium sorbate at a pH of about 4.2, for about 20 seconds. Excess of the agarose-sterol solution was allowed to drip and the flower bulbs were kept at room temperature until gelation of the agarose on the surface of the bulb was completed. Later it was dried in hot air tunnel for about 5 minutes until the dried hydrocolloid coating contained about 5% moisture.

The bulbs were then stored for 5 months in an open shed. At the end of the storage period, it was found that the coating reduced the percent of infections caused by Aspergillus, Botrytis and Fusarium spp. on the surface of the bulbs by about 25% of control and that the weight loss was reduced by about 15%, compared to uncoated flower bulbs, for a storage of about 5 months. These results were achieved because of the high heat capacity of the agarose solution, the good adhesion and the effectiveness of the potassium sorbate at the storage conditions.

The dry film contains 93% agarose, 1.8% sterol, 0.2% potassium sorbate and 5% water.

The reduction in weight loss improved the size and appearance of the flower produced from the coated bulbs, as compared with uncoated bulbs.

EXAMPLE 6

Dry garlic bulbs (coated about 3 months after harvest) were immersed in a warm solution (60–70° C.), containing 2% gellan gum (Kelcogel), 0.01% β-stigmasterol, 0.5% lecithin and 0.5% Locust Bean Gum for about 15 seconds. Excess of the gellan-sterol-lecithin-adhesive agent solution was allowed to drip and the garlic bulbs were then immersed in 0.2% (w/w) MgCl$_2$ solution. The gelled layer coating the garlic was then dried by a blow of warm air. The dried bulbs were then stored at ambient temperatures for 40 days.

For comparative purposes, similar dry garlic bulbs were treated in same procedure with a 2% gellan gum solution devoid of sterol, lecithin and Locust Bean Gum.

The dry film contains 47.8% hydrocollolid, 11.9% lecitin, 11.9% Locust Bean Gum, 0.4% stigmasterol and 28% water.

The gellan-sterol-emulsifier-adhesive coating was found to reduce the weight loss of garlic, as compared to gellan coating, by about 20%. For the gellan coating, about 4.2% moisture loss was measured, after 40 days of storage, whereas 3.36% water loss was measured for the bulbs coated with the gellan-sterol-lecithin-LBG combination.

EXAMPLE 7

Hard yellow cheese with pH of 5.2, 57% dry matter, 30% fat, 1.6% salt was immersed first in 2% calcium lactate solution and then in 1.5% sodium alginate solution which was previously dissolved in milk. Similar experiments were performed for K-carrageenan with the addition of 1% KCl on the basis of full milk (3% fat).

After immersion for 60 seconds in the calcium lactate solution, the cheese was immersed in the alginate for about 30 seconds and then the excess of the solution was allowed to drip for one minute. Drying was done by blowing air at 30° C. for 2 minutes and then 20° C. for additional 5 minutes. Cheese was kept at 4° C. and relative humidity of 75%. In the case of the carrageenan, coating was done at 70° C. The cold cheese immediately lowered the temperature of the coating which was later dried in a simmilar way to the alginate. After 17 days the weight loss of the coated cheese was 3.9% less than the weight loss of the uncoated cheese. Also the color of the coated cheese was better (similar to natural) compared with the uncoated system. In a separate experiment, the same composition for coating was used except for the addition of 0.2% Tween 80 to the sodium alginate or carrageenan solution. It was found that these coatings are smoother and better filled the natural roughness of the cheese surface.

EXAMPLE 8

Squalene was used to protect grapefruits. An alginate and squaline solution was prepared containing 2% sodium alginate and 0.2–0.5% squalene, and grapefruits were immersed in this solution for 30 seconds followed by immersion in a 2% calcium chloride bath. The wet gel film was dried under a continuous flux of warm air to produce a positive dried gel film coatingto provide a protective gel coating which reduced chilling injury when applied to the grapefruit.

A comparative solution was prepared using only an alginate solution without the squalene, and other grapefruits were coated with this comparative solution and similarly dried.

In a comparative peel test, it was found that the alginate-squalene coating adhered better to the grapefruit skin than did the alginate film, suggesting that the chemical similarity, with squalene in both the coating film and the natural peel of the fruit, helped to achieve a stronger attachment and adhesion between the gel film and the fruit.

EXAMPLE 9

Easy peelers of cultivar "Nova" of *Citrus Reticula Blanco* were harvested from a local orchard. They were washed in water and then dried. A solution was prepared of xanthan-LBG together with a citrus essential oil (0.5–1.5%) and a coating of this solution was applied by rubbing 340 μL onto the fruit surface. The coated fruits were then dried with an air blower at 25° C. to provide a protective dried gel coating.

The so-protected fruit was stored at 4° C. and 68% RH for thirty days, then seven days at 21° C. and 71% RH. The stored fruit was then compared with controls. The essential oil coated fruits were found to be superior in terms of taste, containing less ethanol and acetaldehyde.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above i.e., other means or steps for carrying out the same function can be used; and it is intended that such expressions be given their broadest interpretation.

What is claimed is:

1. A protective coating for a food and/or agricultural product comprising:
    50–95% of dried hydrocolloid gel;
    0.2–50% of one or more natural protective compounds isolated from the surface of said product, wherein said one or more protective compounds are selected from the group consisting of a hydrocarbon, a wax, a sterol, a fat and a protein;
    4–30% of water; and
    optional additives selected from the group consisting of emulsifying agents, preservative agents, adhesive agents, cross-linking or gelation inducing agents, and surface-tension reducing agents.

2. A protective coating for a food and/or agricultural product according to claim 1 comprising sn emulsifying agent.

3. A protective coating for a food or agricultural product according to claim 2, further comprising at least one of ethanol, a preservative agent and an adhesive agent.

4. A protective coating for a food and/or agricultural product according to claim 1 comprising a preservative agent.

5. A protective coating for a food and/or agricultural product according to claim 1 comprising an adhesive agent.

6. A method for producing a protective coating for a food and/or agricultural product comprising:
    applying to the external surface of said product:
    (1) a gelation solution comprising a hydrocolloid; and
    (2) a solution comprising a gelation inducing agent when said hydrocolloid undergoes gelation only in the presence of a gelation inducing agent;
    whereby said hydrocolloid forms a gel;
    wherein at least one of said solutions further comprises at least one natural compound isolated from the surface of said product or a protective compound substantially equivalent thereto, wherein said at least one natural compound or protective compound is selected from the group consisting of a hydrocarbon, a wax, a sterol, a fat and a protein.

7. A method for producing a protective coating for a food and/or agricultural product according to claim 6 comprising applying to the external surface of said product said gelation solution comprising said hydrocolloid together with said at least one natural compound or said protective compound, wherein said hydrocolloid is one which does not require a gelation inducing agent to form a gel, and wherein said solution (2) is not applied.

8. A method for producing a protective coating for a food and/or agricultural product according to claim 6 comprising applying to the external surface of said product (1) said gelation solution comprising said hydrocolloid wherein said hydrocolloid is one which undergoes gelation only in the presence of a gelation inducing agent, and (2) said solution comprising said gelation inducing agent.

9. A method according to claim 8 wherein the gelation solution comprising the hydrocolloid is applied to the external surface of the food or agricultural product first, and the solution comprising the gelation inducing agent is applied thereafter.

10. A method according to claim 8 wherein the gelation inducing agent is applied to the external surface of the food or agricultural product first, and the gelation solution comprising the hydrocolloid is applied thereafter.

11. A method for producing a protective coating for a food and/or agricultural product according to claim 6 wherein the gelation solution further comprises an adhesive agent.

12. A method according to claim 11, wherein the gelation solution further comprises at least one of an emulsifying agent, a preservative agent and ethanol.

13. A method according to claim 6 wherein the gelation solution further comprises an emulsifying agent.

14. A method according to claim 6 wherein the natural compound or the protective compound is selected from the group consisting of a sterol a hydrocarbon and a wax.

15. A method according to claim 6 wherein the external surface of the food and/or agricultural product is further treated with a surface tension reducing agent by pre-immersion in said surface tension reducing agent or by including said surface tension reducing agent in said gelation solution.

16. A food and/or agricultural product coated by a protective coating comprising a matrix of
    20–95% gelled and optionally cross-linked dried hydrocolloid gel;
    0.2–50% of at least one natural compound isolated from the surface of said product or a protective compound substantially equivalent thereto, wherein said at least one natural compound or said protective compound is selected from the group consisting of a sterol, a hydrocarbon, a wax, a fat and a protein;
    4–30% of water; and
    optional additives selected from the group consisting of emulsifying agents, preservative agents, adhesive agents, cross-linking or gelation inducing agents, and surface-tension reducing agents.

17. The food or agricultural product according to claim 16 wherein the coating comprises 40 to 95% hydrocolloid and 0.3 to 12% sterol.

* * * * *